(12) United States Patent
Chen (10) Patent No.: US 6,174,733 B1
(45) Date of Patent: Jan. 16, 2001

(54) DETECTION OF PATHOGENS USING A COLUMN DEVICE WITH A SAMPLE CONTAINING A CONTROL

(75) Inventor: Hai-Shene Chen, Toronto (CA)

(73) Assignee: ACGT Medico Inc., Toronto (CA)

( * ) Notice: Under 35 U.S.C. 154(b), the term of this patent shall be extended for 0 days.

(21) Appl. No.: 09/093,532

(22) Filed: Jun. 8, 1998

(30) Foreign Application Priority Data

Jun. 9, 1997 (GB) ................................................... 9711941

(51) Int. Cl.[7] ........................ G01N 33/566; G01N 33/53; C12Q 1/68; C07H 19/00; B01D 15/08
(52) U.S. Cl. ............................... 436/501; 435/6; 435/7.1; 536/22.1; 536/23.1; 536/24.3; 536/24.31; 536/24.32; 536/24.33; 210/635; 210/636; 210/658; 210/663; 422/100; 436/501
(58) Field of Search ........................ 435/6, 7.1; 536/23.1, 536/22.1, 24.3, 24.31, 24.32, 24.33; 210/635, 656, 658, 663; 422/100; 436/501

(56) References Cited

U.S. PATENT DOCUMENTS 5,160,701 * 11/1992 Brown, III et al. .................... 422/56
5,804,384    9/1998 Muller et al. .
5,876,918 *  3/1999 Wainwright et al. .................... 435/4
5,922,533 *  7/1999 Vallari et al. ............................. 435/5

FOREIGN PATENT DOCUMENTS

| 0 387 696 A3 | 8/1990 | (EP) . |
| 0 605 828 A1 | 7/1994 | (EP) . |
| 0 780 479 A2 | 6/1997 | (EP) . |
| 0 846 776 A2 | 10/1998 | (EP) . |
| 2 283 569 | 10/1995 | (GB) . |
| 2 324 370 | 10/1998 | (GB) . |

* cited by examiner

*Primary Examiner*—W. Gary Jones
*Assistant Examiner*—Jeffrey Siew
(74) *Attorney, Agent, or Firm*—Yi Li (57) ABSTRACT

Methods are disclosed for detecting the presence of at least two predetermined known materials in a test sample. At least one of the predetermined known materials is a control material. The test sample is introduced into a test column which has a snare for each predetermined known material. Each snare has a capture material specific to the associated predetermined known material, and the capture material will bind with the associated predetermined known material to form a bound material. The test column is then washed to remove any materials which have not been bound to the capture materials. Finally, the presence of bound materials is detected on each of the snares. The method is useful for pathogens, DNA and RNA.

15 Claims, 9 Drawing Sheets

DETECTION OF PATHOGENS USING A COLUMN DEVICE WITH A SAMPLE CONTAINING A CONTROL

FIELD OF THE INVENTION

The present invention relates to the detection materials in small concentrations, especially the detection of pathogens. In particular it relates to the detection of proteins, DNA and RNA in serum.

BACKGROUND TO THE INVENTION

Known manual pathogen detection methods in research and clinical laboratories tend to have low accuracy, low sensitivity to pathogens and are subject to human error, both in carrying out the methods and in interpreting the results. Other methods, e.g. culturing methods, are not suitable for many pathogens. For example, tuberculosis has a very slow growth rate, which makes detection not easy or even not possible.

One immunologic method, which identifies an organism with a known antiserum, is widely used for pathogen detection. The accuracy of the method is relatively high but the sensitivity is relatively low, e.g. it needs about one million antigen-antibody complexes to clearly indicate the results. There are a number of other disadvantages of this method, which are known.

In a standard enzyme ELISA method for immunoassay, a tray with a plurality of wells, e.g. 96 wells, containing appropriate antibodies, is used. One of the wells is used as a positive control (with a positive antigen), while the remaining wells are used for testing patient's sera. After addition of the serum samples, the wells are washed and a second antibody, which carries an enzyme, is added to the wells. After washing again, a substrate is added. The substrate and enzyme react, with a colour reaction. The colour yield from the reaction is indicative of the presence of the pathogen. The method is rife with possibilities for error. Human error can lead to some wells being washed twice or not at all, having reagents added twice or not at all, or wells being inadvertently contaminated with extraneous materials. For example, overwashing tends to flush all the components and create a false negative result, while an incomplete wash will provide detection from non-binding materials and yield false positive results. The control well can give no assurance that the results from any other well is indicative of the presence or otherwise of the pathogen under investigation. Additionally, colour differences from well to well give additional uncertainties with respect to interpretation of the results.

Most of the previous tests are demanding of time, skill and concentration. So much so, that in many jurisdictions the number of tests that can be conducted by one technician is limited by regulation. This serves to raise the cost of testing, as it is so labour dependent.

For all the above reasons, and more, a new method of detecting pathogens is desirable, which is accurate, reproducible, and is sensitive to determining if there is an error in the method.

SUMMARY OF THE INVENTION

The present invention provides a method for detecting the presence of at least two predetermined known materials in a test sample, wherein at least one of the predetermined known materials is a control material, wherein the method comprises:

a) introducing the test sample, which contains at least one control material, into a test column which has a snare for each predetermined known material, each snare having a capture material specific to the associated predetermined known material, which will bind with the associated predetermined known material to form a bound material;

b) washing the test column to remove any materials which have not been bound to the capture materials; and c) detecting the presence of bound materials on each of the snares.

In one embodiment, the predetermined known materials, which are not control materials, are pathogens.

In another embodiment, step c) comprises adding a label material for each of the bound materials to form labelled bound materials and then detecting the labelled bound materials.

In a further embodiment, the method is for detecting the presence of at least two predetermined known DNA materials, wherein the capture materials are single strand capture DNA materials and the test sample has been denatured so that any predetermined known DNA materials are in single strand form prior to addition to the test column, and detection of the bound materials is accomplished by adding a label material for each of the bound materials to form labelled bound materials and then detecting the labelled bound materials.

In another embodiment, the label material for the control DNA material and the non-control DNA material is selected such that the label material is a single label material.

Another aspect of the invention provides a method for detecting the presence of a pathogen, comprising the steps of:

i) adding a sample, which contains at least one control material, to a column which has at least one control snare and at least one test snare, each of the control snares having thereon a first capture antibody for binding to the control material, and each of the test snares having thereon a pathogen capture antibody for binding to the pathogen for which detection is being sought, so that the control material binds with the first capture antibody to form a bound control material, and any pathogen present binds with the pathogen capture antibody to form a bound pathogen;

ii) adding a wash solution to the column to remove any unbound control material and any unbound pathogens;

iii) adding sufficient primary antibodies to the column, to bind with the control material and any bound pathogens, said primary antibodies having labels thereon;

iv) adding a wash solution to the column to remove any unbound primary antibodies;

v) adding a substrate which reacts with the labels to give off a detectable signal; and vi) detecting any detectable signals from the labelled and bound control material and from any labelled and bound pathogen.

In one embodiment, the substrate and label are selected to give off a chemiluminescent signal.

In another embodiment, the substrate and label are selected to give off a fluorescent signal.

A further aspect of the invention provides a method for detecting the presence of a DNA in a sample, comprising the steps of:

i) denaturing the predetermined known DNA materials;

ii) adding a sample, which contains at least one denatured control DNA segment, to a column which has at least one control snare and at least one test snare, one of the control snares having thereon a first control single strand capture DNA segment for binding to the denatured control DNA segment, and one of the test snares having thereon a test single strand capture DNA segment for detecting the denatured test DNA segment for which detection is being sought, so that the denatured control DNA segment binds with the first control single strand capture DNA segment to form a double strand control DNA segment, and any denatured test DNA present binds with the test single strand capture DNA segment to form a double strand test DNA segment;

iii) adding a wash solution to the column to remove any unbound DNA;

iv) adding S1 nuclease to the column to destroy any single strand DNA;

v) adding a wash solution and a denaturing solution to the column to re-form the first control single strand capture DNA segment and the test single strand capture DNA segment;

vi) adding DNA probes to provide detectable labels for the first control single strand capture DNA segment and the test single strand capture DNA segment formed in step v);

vii) adding a wash solution to the column to remove any unbound DNA probe;

viii) adding a substrate which reacts with the labels to give off detectable signals; and ix) detecting any signals from the control and test snares.

In yet another embodiment the method comprises:

i) preparing a positive control DNA material from a DNA material for which detection is sought, by a process selected from the group consisting of a) inserting a control DNA sequence into the DNA material at a predetermined scission point in the first DNA material and b) removing a small fragment of DNA from the first DNA material at a predetermined scission point;

ii) denaturing a test sample which contains at least the positive control DNA material;

iii) adding the sample, which contains denatured positive control DNA material, to a test column which has at least one control snare and at least one test snare, one of the control snares having thereon a first control single strand capture DNA segment for binding to a portion of the positive control DNA material, and one of the test snares having thereon a test single strand capture DNA segment for detecting denatured test DNA segment for which detection is being sought, so that the positive control DNA material binds with the first control single strand capture DNA segment to form a bound positive control DNA material which also has an unbound single strand segment, and any denatured test DNA present binds with the test single strand capture DNA segment to form a bound test DNA material which also has an unbound single strand segment;

iv) adding a wash solution to the column to remove any unbound DNA;

v) adding DNA probes to provide detectable labels for attachment to the unbound segment of the bound positive control DNA material and the unbound segment of the bound test DNA material formed in step iii);

vi) adding a wash solution to the column to remove any unbound DNA probe;

vii) adding a substrate which reacts with the labels to give off detectable signals; and viii) detecting any signals from the control and test snares.

In yet another embodiment, the method is for detecting the presence of at least one predetermined known RNA material in a test sample, wherein the test sample contains at least one predetermined known control DNA material, and wherein the test sample has been denatured so that any RNA and DNA materials are in single strand, wherein the method comprises:

In one embodiment, in the RNA method a second control DNA material is also present, in which the second control DNA material has a partial DNA sequence match with the associated capture DNA material, so that in step a) the second control DNA material forms a partially bound DNA material with single strands attached thereto, and so that in step c) the single strands attached to the partially bound material are destroyed, leaving partially bound DNA material, and so that in step d) a partial DNA sequence single strand material is formed by denaturing.

The present invention also provides a column for analysis of at least one pathogen in which the column has at least two snares, one of said snares having thereon a first control capture material for detecting the presence of a first control material, and the other of said snares having thereon a pathogen capture material for detecting a pathogen for which detection is being sought.

In one embodiment, the snares are separated longitudinally along the column.

In another embodiment, the snares are separated radially about a longitudinal axis of the column.

In yet another embodiment, column has a snare having thereon a first control material, and a plurality of snares each having thereon a pathogen capture material wherein the pathogen capture materials are different from one another.

In a further embodiment, the column has a snare-having thereon a first control material, at least one snare having thereon a pathogen capture material and a snare having a second control material for detecting the presence of a second control material.

In another embodiment, the capture materials are capture antibodies.

In a further embodiment, the capture materials are single strand DNA materials.

In yet another embodiment the presence of the first control material and the pathogen material may be detected by the same detection material.

In another embodiment, the column has a longitudinal axis and comprises at least two chambers, at least one of the chambers containing a snare with a control capture material, and at least one of the chambers containing a pathogen capture material, each of said chambers having connecting means to connect the chambers in a predetermined sequence along the axis.

In yet another embodiment, each chamber has a different cross-sectional areas of all other chambers.

In a further embodiment, each chamber has a different diameter from the diameters of all other chambers.

In yet another embodiment, the column has an additional chamber with a snare without a capture material thereon.

In another embodiment, the column has a longitudinal axis and comprises at least one chamber, each chamber containing at least one snare with a control capture material and at least one pathogen snare each with a pathogen capture material, wherein the snares are spaced radially about the longitudinal axis.

In another embodiment, the first control material is albumin.

In another aspect of the invention, there is provided a kit which comprises i) a column for analysis of at least one pathogen in which the column has at least two snares, one of said snares having thereon a first control capture material for detecting the presence of a first control material, and the other of said snares having thereon a pathogen capture material for detecting a pathogen for which detection is being sought, ii) reagents for detecting the presence of the materials selected from the group consisting of a) reagents for detecting the presence of the control pathogen and the test pathogen, and b) reagents for detecting the presence of the first control capture material and the pathogen capture material after the first control capture material and the pathogen capture material have been bound and then unbound from the first control material and the pathogen material.

In one embodiment, the kit also includes wash solutions for removing excess reagents from the column.

Another aspect of the invention provides an apparatus for detection of at least two predetermined known materials in a sample, at least one of said predetermined known materials being a control material, said apparatus comprising:

a) a sample addition station for adding a sample to a testing column;

b) at least one reagent addition station, each reagent addition station being associated with a washing station;

c) a detection station for detection of the predetermined known materials which may be in the testing column;

d) conveying means for conveying the testing column from the sample addition station, sequentially past each reagent addition station and washing station and thence to the detection station.

In one embodiment, each reagent addition station has delivery means for delivering a measured quantity of reagent to the column and each washing station has delivery means for delivering a measured quantity of washing solution to the column.

In another embodiment, the column has a longitudinal axis and a plurality of snares, each for capturing a predetermined known material, and the detection station has a plurality of detectors for detecting the presence of the predetermined materials at the snare locations along the longitudinal axis.

In a further embodiment, the detection station has two detectors for detecting different control materials, and a sufficient number of detectors for detecting the predetermined known materials.

In another embodiment, the detectors are laser detectors for detecting chemiluminescence.

In yet another embodiment, the column has a plurality of snare locations in a plane transverse to a longitudinal axis of the column, each snare having means for capturing a predetermined known material, and the detection station has a plurality of detectors for detecting the presence of the predetermined materials at the snare locations.

In a further embodiment, the detectors are for predetermined known materials selected from the group consisting of pathogens, DNA materials and RNA materials.

Another aspect of the invention provides an apparatus for recycling used test columns which have at least one snare with a capture material attached to the snare and a test material attached to the capture material, comprising a) a stripping station for adding a stripping material to the test column, in order to strip the test material from the capture material;

b) a first washing station after each stripping station, for adding a wash material in order to wash stripped test material from the column;

c) a first detection station for detecting the presence of the test material; and d) conveying means for conveying test columns sequentially past each of the stripping station, washing station and detection station.

In one embodiment there is a second stripping station, second washing station and second detection station and the conveying means is for conveying the test column sequentially past each of the second stripping station, second washing station and second detection station after being conveyed past the first detection station.

DETAILED DESCRIPTION OF PREFERRED EMBODIMENTS

Figure 1:
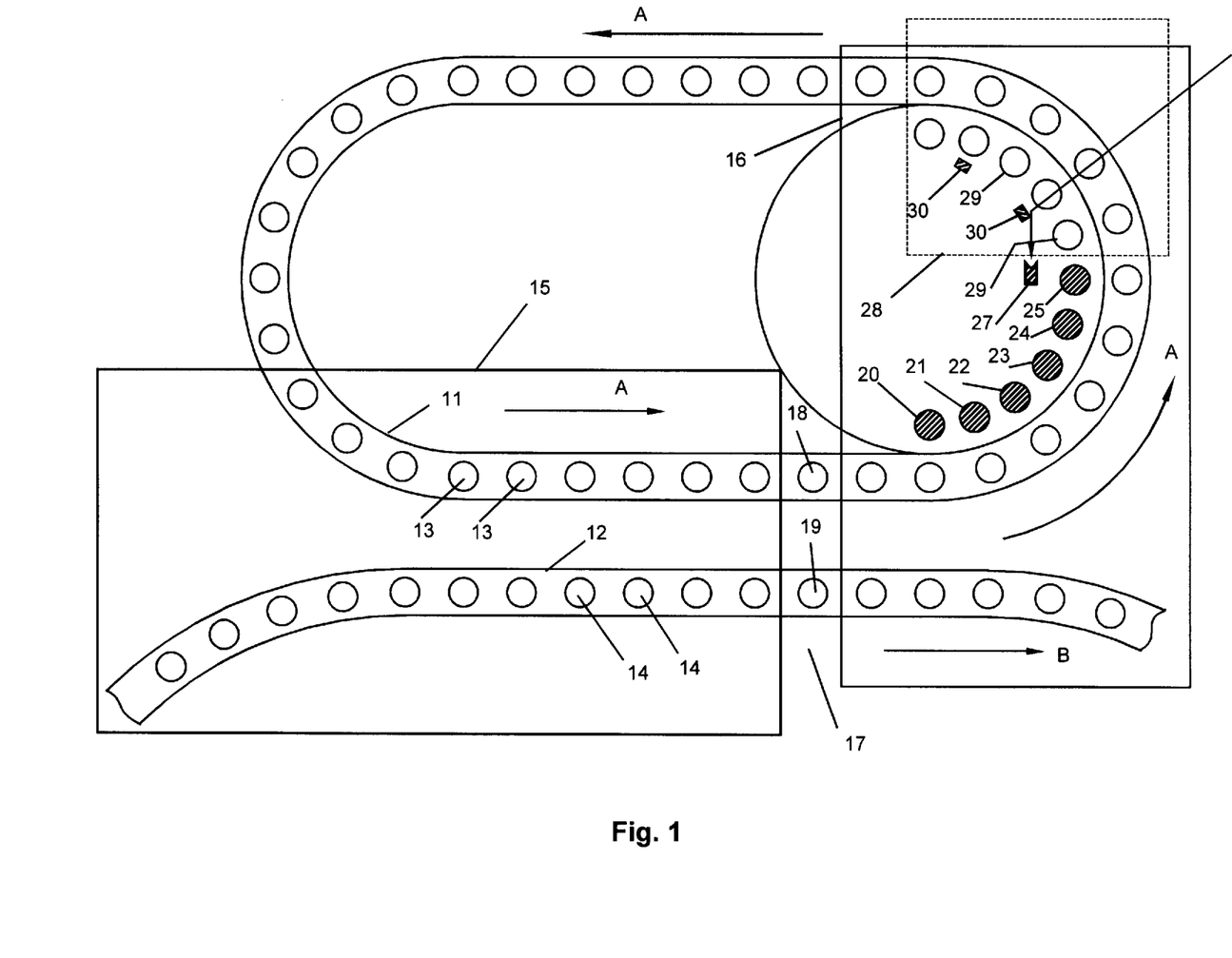
FIG. 1 is a partial general layout of an apparatus for carrying out one embodiment of the present invention.

The apparatus of FIG. 1 comprises a column conveyor 11 and a test tube conveyor 12, each of which has means (not shown) associated therewith for moving the conveyors, generally in the directions shown by arrows A and B. Column conveyor 11 has a plurality of columns 13 which are equidistantly attached to column conveyor 11. Attachment of columns 13 to column conveyor 11 is preferably temporary so that used or defective columns can be removed and replaced. Test tube conveyor 12 has a plurality of test tubes 14, e.g. serum tubes. Preferably the test tubes 14 are equidistantly attached to test tube conveyor 12. Attachment of the test tubes 14 to the test tube conveyor 12 is preferably temporary so that used or defective test tubes can be removed and replaced. The means for moving the conveyors are preferably indexing means (not shown). The conveyors 11 and 12, test tubes 14 and columns 13 are covered within housings 15 and 16, apart from a window 17 which is wide enough to accommodate only one column 18 and an associated test tube 19. The column conveyor 11 and the test tube conveyor 12 are indexed so that only one test tube 19 is adjacent to an associated column 18, when in window 17.

Within housing 16, there are a number of reagent stations, for example reagent stations 20–25, for adding reagents to the columns as the columns index past the stations. At the end of the reagent stations or downstream thereof, there is detector means 27. In the embodiment shown in FIG. 1, there is also a cleaning zone 28. In the cleaning zone there is a series of wash stations 29, possibly stripping stations for stripping any unwanted materials from the column, and associated detectors 30.

It will be understood that instead of a series of wash stations, stripping stations and detector stations, there may be a single wash station, stripping station and detector station and a column is caused to pass the wash station, stripping station and detector station again if any contamination is detected on the first pass of the column past the detector station. This can be accomplished with a rotating table, for example.

Figure 2A:
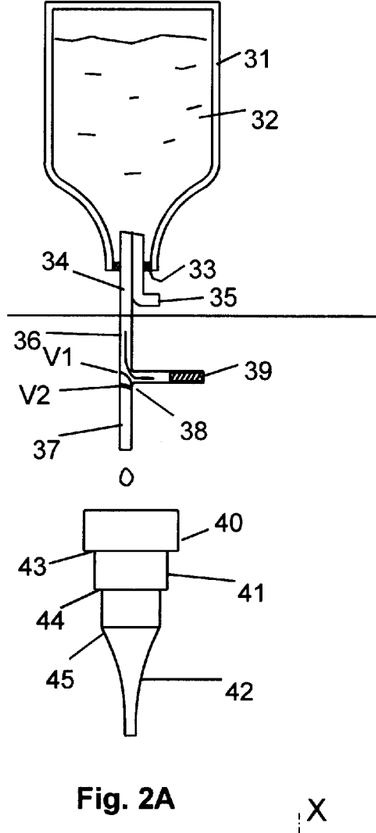
FIGS. 2A and 2B show a reagent delivery station for delivering a reagent to a column.
Figure 2B:
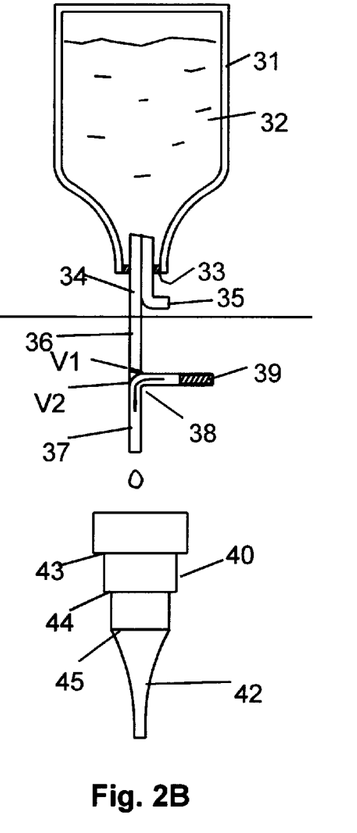

FIGS. 2A and 2B show one type of reagent station and one type of a column. At the reagent station there is a reagent bottle 31 with reagent 32 therein. The reagent bottle 31 has a rubber septum 33 through which a double-hollow needle 34 may penetrate. The double-hollow needle 34 has one tube 35 which is connected to an air supply (not shown). A second tube 36 is connected to a delivery tube 37 by a double valve junction 38. Also connected to double valve junction 38 is a measuring syringe 39. Second tube 36 and delivery tube 37 may be a single tube with a double valve junction therein. Valves V1 and V2 in double valve junction 38 allow reagent 32 to be drawn into measuring syringe 39 and then be expelled from measuring syringe 39 through delivery tube 37. Column 40 is situated just below delivery tube 37 so that reagent may be transferred, e.g. by gravity, to column 40. Alternatively there may be a liquid-tight connection between delivery tube 37 and column 40. The reagents may be urged through the columns by means of pressure from the top or vacuum attached to the discharge tube.

Column 40 comprises a column casing 41 and a discharge tube 42. Column casing 41 houses three snares 43, 44 and 45, which are spaced apart from one another. The snares are spaced apart along longitudinal axis X—X of column 40 (see FIG. 3). Although three snares are shown in FIGS. 2A and 2B, there should be at least two snares in a column. At least one of the snares is used for detecting a control material, and at least one of the snares is used for detecting the presence or otherwise of a material in a test sample. Snares 43–45 may be made from any suitable material for attaching a capture material as will be explained in more detail hereinafter. Typically the snares are made from a material with high surface area, e.g. sintered glass, sintered plastic, glass fibre, beads, chips, granules. The snares may sometimes be referred herein as glass frits or a fibre chips. The column casing adjacent to the snares are preferably light transparent, for better detection of chemiluminescent or other chemical reaction.

It is preferable that the snares be in a particular order, so that there may be positive identification of any reaction at a particular snare position. Clearly, it is important that detection of any reaction be identified with a particular capture material. For example, it is important that detection of any reaction with a control capture material e.g. albumin, be positively identified with that control capture material and not with any other capture material, e.g. tuberculosis capture material. For this reason it is preferable that there be means to ensure that the order of the snares and their associated capture materials follows a predetermined order.

The column 40 may take any convenient shape. In the FIGS. 2A, 2B, 3, 5A to 5C, column 40 is a step-shaped tube. Such a shape makes it necessary to make snares 43, 44 and 45 to be of different diameters. As will be described in more detail hereinafter, each of the snares may have a different capture antibody attached thereto. As described in general above, it may be important that a snare with a first capture antibody always be placed in the top position 43. Making snare 43 in a larger diameter than the other snares ensures that snare 43 cannot be placed in the position reserved for snare 44 or snare 45. Conversely, making a snare 45 in small diameter, with a different capture antibody to the capture antibody on snare 43, ensures that snare 45 cannot be placed in the position of snare 43 or 44. Obviously this is helpful in ensuring that the snares are correctly placed in the column. Of course, columns with correctly placed snares may be accomplished in other ways and so the stepped-tube arrangement shown in FIGS. 2A, 2B, 3, 5A to 5C is not essential. As will be apparent, the column may have a circular cross-section, a square cross-section or other suitable shape.

As will be described hereinafter at least one of the snares, e.g. 43 is used as a control. In some situations a second snare, e.g. 45 is also used as a second control, as will be described in reference to use of the columns and apparatus. The third snare, e.g. 44, is for testing for presence of a particular chemical from a sample in a test tube, e.g. a pathogen in a patient's serum.

In FIG. 2A, the upper valve V1 of double-valve junction 38 is open and the lower valve V2 is closed, to allow a measured amount of reagent to be drawn into measuring syringe 39. In FIG. 2B, the upper valve V1 of double-valve junction 38 is closed and the lower valve V2 is open, to allow the measured amount of reagent in measuring syringe 39 to be expelled through delivery tube 37.

Figure 3:
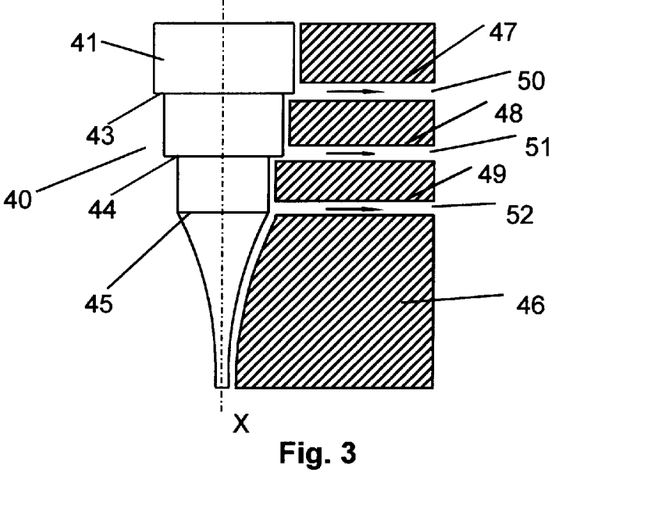
FIG. 3 shows a detector for detecting a signal from a column.

FIG. 3 shows column 40 adjacent to detector means. In the embodiment shown, in order to avoid false readings, detector block 46 is shaped to accommodate the shape of column casing 41. Detector block 46 has channels 47, 48, 49 for allowing any signals emanating from snares 43, 44, 45 to pass to detectors 50, 51 52, respectively. Another advantage of the stepped column casing as shown in FIG. 3 is that signals from each of the snares are prevented from filtering through to an adjacent detector channel. Although UV detectors may be used in certain instances, laser detectors are preferred.

Some reactions are chemiluminescent and detection of the chemiluminescence may be determined directly from light emanating from the snare, as implied from the positioning of channels 47–49 in FIG. 3. However, sometimes it may be necessary to measure the light emanating at an angle from the top surface of each snare. Accordingly, the channels would then be angled to guide such light to an appropriate detector.

Other reactions may require a different detection system. For example, it may be necessary to have a light source for detecting certain reactions, as will be understood by those skilled in the art. In addition, columns different from those of FIG. 2A may require different arrangements for the detection apparatus, as will be described hereinafter.

Although FIG. 3 shows a means, for example, for minimizing cross-over of light from snare 43 to channel 48, if reaction times are in the order of milliseconds and there is a substantial time interval between reactions from adjacent snares, it may not be as critical to prevent light cross-over from one detector to another.

Signals from the detectors may be displayed in a number of ways. For example, the signals may be displayed graphically on paper or on a monitor. The signals may also be manipulated to assess the concentration of pathogens on the various snares. The data from the signals may be stored electronically and then retrieved either locally or remotely. In addition to the data, software can be used to provide information concerning the tests performed and thus enhance the viewer's understanding and interpretation of the results. One of the advantages of remote access to the results is that a doctor who requests the tests may review the raw data both rapidly and directly, without requiring the assistance of and interpretation by a technician. Because there is at least one control test in each column, the doctor can immediately assess whether the tests have been done correctly and thus have a high degree of confidence in any result which shows the presence or absence of the pathogen under consideration. Additionally, because the tests can be conducted so rapidly, a doctor may be able to have tests performed at relatively short time intervals and soon thereafter be able to see if the concentration of pathogen is increasing or decreasing.

Figure 4:
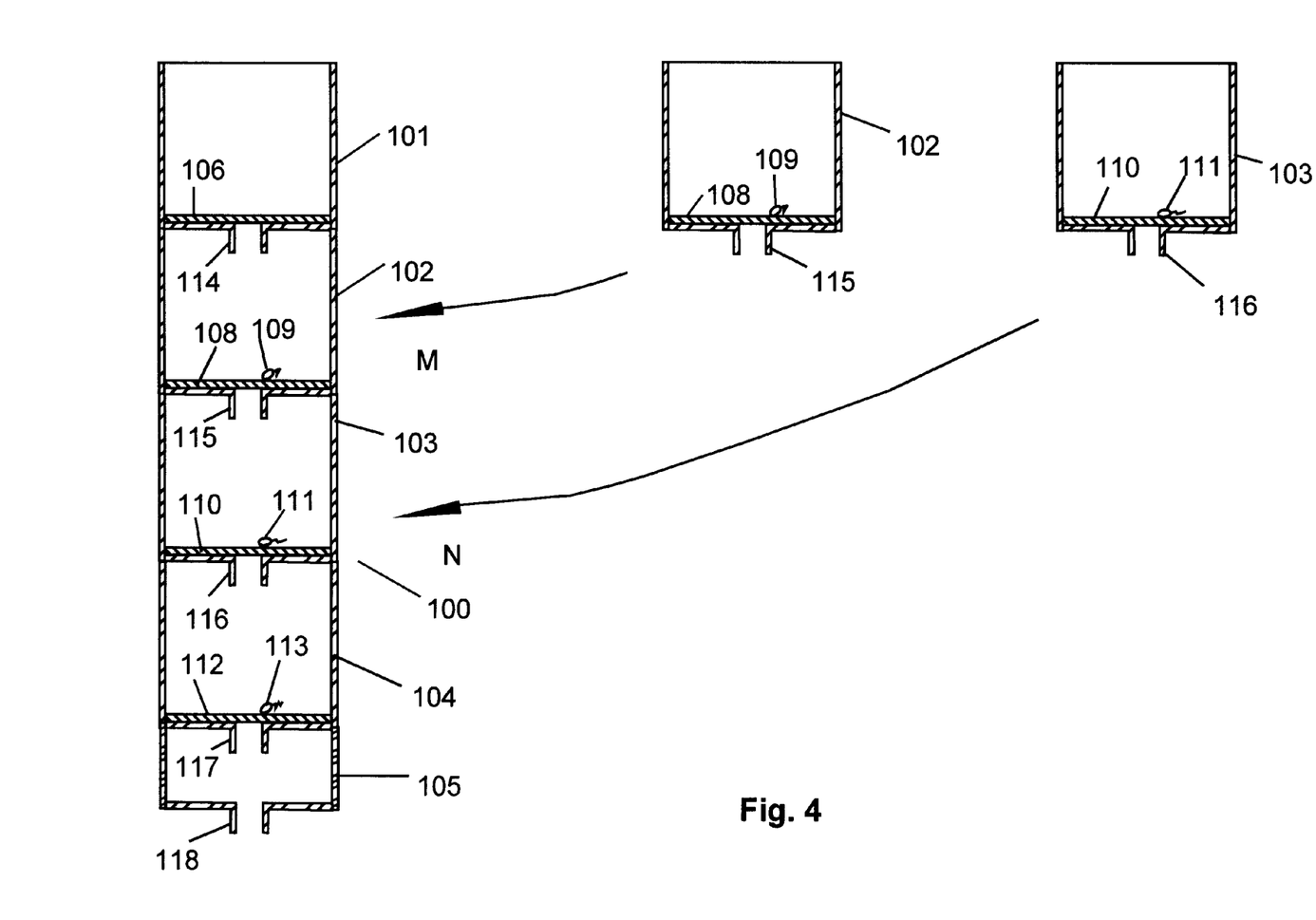
FIG. 4 shows a column made with four chambers.

Another arrangement of the column is shown in FIG. 4. Column 100 is constructed from four chambers 101, 102, 103 and 104 and a discharge chamber 105. Discharge chamber 105 has a discharge spout 118. Chambers 102 and 103 are shown to the right of completed column 100, with arrows M and N to show the placement of chambers 102 and 103 in the column. There are means (not shown) to assure that chamber 102 can only be connected to the bottom of chamber 101, that chamber 103 can only be connected to the bottom of chamber 102, and that chamber 104 can only be connected to the bottom of chamber 103.

In the embodiment shown in FIG. 4, chamber 101 has a drain 114, a snare 106 which has no capture material thereon. Chamber 102 has a drain 115, and a snare 108 with a first control capture material 109. Chamber 103 has a drain 116 and a snare 110 with a pathogen capture material 111. Chamber 104 has a drain 117, and a snare 112, with a second control capture material 113. The significance of the four chambers with their associated capture materials will be described hereinafter, particularly in relation to a pathogen detection method using DNA.

In some countries, used columns must be discarded rather than being reused, whereas in other countries reuse of columns is permitted. In situations where reuse is permitted, an automated cleaning process is preferred in order to assure that the columns are not contaminated or otherwise inoperative. In such a process, the used column is washed with a reagent that destroys everything except the capture materials on the snares. After such washing, the column is tested for the presence of unwanted materials. If there are still unwanted materials on the column, then further washing and detection sequences are carried out. If, after a number of washings, a particular column is still not clean, the column is discarded and replaced by a new column.

Figure 5A:
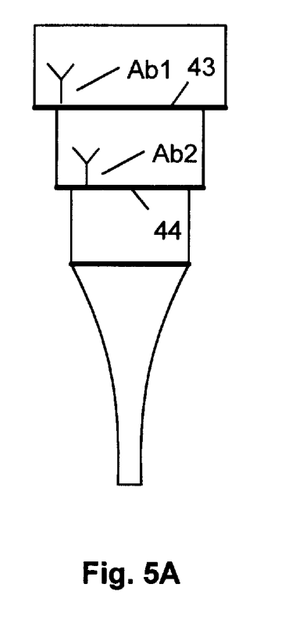
FIGS. 5A, 5B and 5C show a process of the present invention, schematically.
Figure 5B:
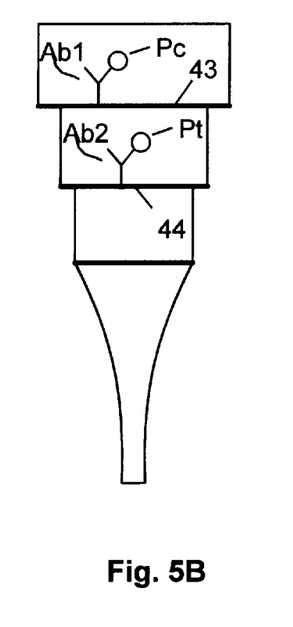

One process falling within the scope of the invention is now described with respect to protein pathogen detection in a serum sample. FIGS. 5A, 5B and 5C generally show the process in simplified terms, in which there is detection of a control protein Pc, e.g. albumin, and a protein Pt whose presence is being tested for, e.g. a tuberculosis protein. The control protein Pc is present in the serum and it is not known whether the tuberculosis protein Pt is present. With reference to FIG. 1, therefore, the control protein Pc is already inherently in the sample in test tube 19 or had been deliberately added beforehand. Snare 43 is a sintered glass frit which has a first capture antibody Ab1 attached thereto, and snare 44 is a sintered glass frit which has a second capture antibody Ab2 attached thereto, as shown in FIG. 5A. Snares 43 and 44 are in the same column and are indexed to the window 17, so that the column is in the position 18 (see FIG. 1). As indicated, the serum which is in test tube 19 contains the control protein Pc. For the purposes of this illustration, it is assumed that the protein Pt which is to be tested for, e.g. a tuberculosis pathogen protein, is present. A technician transfers an aliquot of serum from test tube 19 into the top of column 18 and the conveyor then indexes the conveyors so that the column is moved to the first reagent station. As it does so, the serum travels through snares 43 and 44. Control protein Pc binds to the first capture antibody Ab1 on snare 43, and the pathogen protein Pt binds to the second capture antibody Ab2 on snare 44, as shown in FIG. 5B. At the first reagent station, a wash is administered to the column. The purpose of the wash is to remove any excess serum, including any unbound control protein Pc and test protein Pt.

It will be understood that transfer of serum to the column may also be automated. At the time of transfer of the serum to the column, the correlation of the identity of the serum test tube and the corresponding column are noted, either by the technician, e.g. by typing identification numbers into a computer, or by automatic methods such as bar coding of test tubes and columns.

Figure 5C:
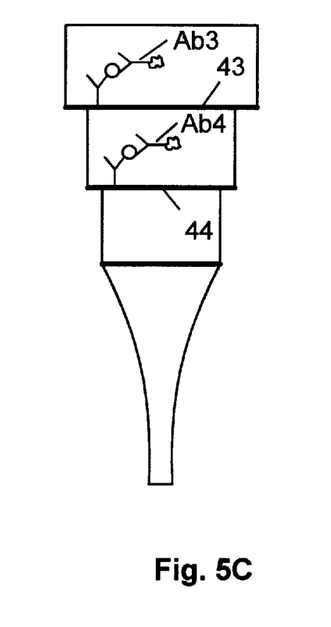

After washing at the first reagent station, the column is then indexed to a second reagent station. At the second reagent station, a primary antibody Ab3 which will bind to the control protein Pc, is added to the column. Primary antibody Ab3 has, for example, a chemiluminescent label. After indexing to a third reagent station, a primary antibody Ab4 which will bind to the test protein Pt, is added to the column, as shown in FIG. 5C. Primary antibody Ab4 also has, for example, a chemiluminescent label. The column is then indexed to a fourth reagent station which is a wash station. The wash removes any excess primary antibodies Ab3 and Ab4. It is preferable that antibodies Ab3 and Ab4 are the same, in which case only one reagent station is required for the primary antibody.

The column is then indexed to a fifth reagent station which is also adjacent to a detector block. At the fifth reagent station a trigger solution is added to the column. The trigger solution reacts with the labels of the primary antibodies Ab3 and Ab4. Assuming that the reactions are chemiluminescent, there are emanations of light from each of the snares 43 and 44. The light signal from snare 43 is then detected by detector 50 and the light signal from snare 44 is detected by detector 51. Light from snare 43 indicates the presence of the control protein Pc on the snare and light from snare 44 indicates the presence of the pathogen protein Pt on the snare.

It will be appreciated from the above discussion that if there is no pathogen protein Pt in the serum, then obviously there can be no binding of such protein to capture antibody Ab2. Thus there would be nothing for primary antibody Ab4 to react with and so there would be no chemiluminescence detected by detector 51.

The advantage of having the control protein Pc in the serum sample is that if there is no signal detected by detector 50 after adding the trigger solution, then it can be reasonably assumed that the serum sample was not added to the column. However, if there is a signal from the control protein Pc, then the person analyzing the results can be reasonably assured that a negative response from snare 44 truly indicates that there is (within the detection limit of the detector) no pathogen Pt present in the serum.

The control protein may be a protein that is always present in a serum sample, e.g. albumin, or a control protein may be added deliberately to the serum.

It is sometimes desirable to have a second control protein (P2), which would be used to indicate whether all of the steps in the process have been carried out. For example, snare 45 may have a third capture antibody Ab5 (not shown) thereon. After addition of the serum, with the first control protein Pc and possibly the pathogen protein Pt, and washing of the column, the second control protein P2 may be added. Second control protein P2 would bind to third capture antibody Ab5. Third capture antibody Ab5 may be activated by addition of a primary antibody Ab6 which has a label, e.g. a chemiluminescent label. Now, instead of adding a reagent which only has primary antibodies Ab3 and Ab4 as described in previous paragraphs, a reagent which has primary antibodies Ab3, Ab4 and Ab6 is added to column 40. After washing and addition of a trigger solution, any reaction with primary antibody Ab6 would be detected by detector 52. It should be noted that the second control protein may be added to the column together with the first control protein instead of separately, if desired.

It will be appreciated that if there is no detection of the second control protein P2, it can be safely assumed that the primary antibodies Ab3 and Ab4 were not added to the column. Thus there is a further indication of whether the complete analytical process has been performed properly.

Although described above in relation to detection of pathogens in serum samples, the above method may be adapted for detection of viruses or chemicals such as drugs, carcinogens, explosives, opiates, pollutants, e.g. arsenic, cyanides, benzenes.

Figure 6:
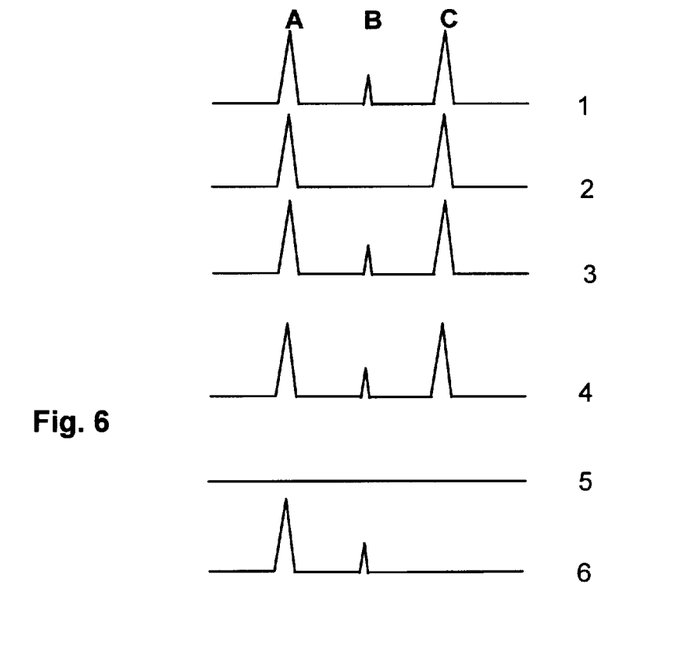
FIG. 6 shows read-outs from six sample columns.

FIG. 6 shows the results of a method used where there are two control snares A and C and a snare B, which is used to detect for the presence of a particular pathogen. In FIG. 6, six sample columns 1–6 were tested. Sample columns 1, 2, 3 and 4 show the presence of both control proteins, thus indicating that the serum is present, and that the correct primary antibodies for the first control and pathogen were added. Sample columns 1, 3 and 4 show the presence of the pathogen in snare B, whereas in sample 2 there is no pathogen detected. Because both the control signals are positive, the operator can be reasonably assured that the lack of a signal for the pathogen, in sample column 2 indicates that there is indeed no pathogen present. In sample 5, neither of the control signals appear, indicating that the sample column never contained any control protein and thus the negative signal for snare B is meaningless.

In sample 6, the second control is not present. This indicates that the correct primary antibodies for detection of the first control and the pathogen were not added. Thus sample 6 gives a false indication of the presence of the first control and the pathogen. Detection of materials on the snares A and B has been detected, which may or may not be the first control and the pathogen. Therefore, sample 6 is also meaningless.

The advantage of the present invention over prior methods is that sample 5 in prior methods may well have been counted as a definite negative, i.e. it is a false negative for snare B and that sample 6 in prior methods may well have been counted as a definite positive, i.e. it is a false positive for snare B.

Figure 7:
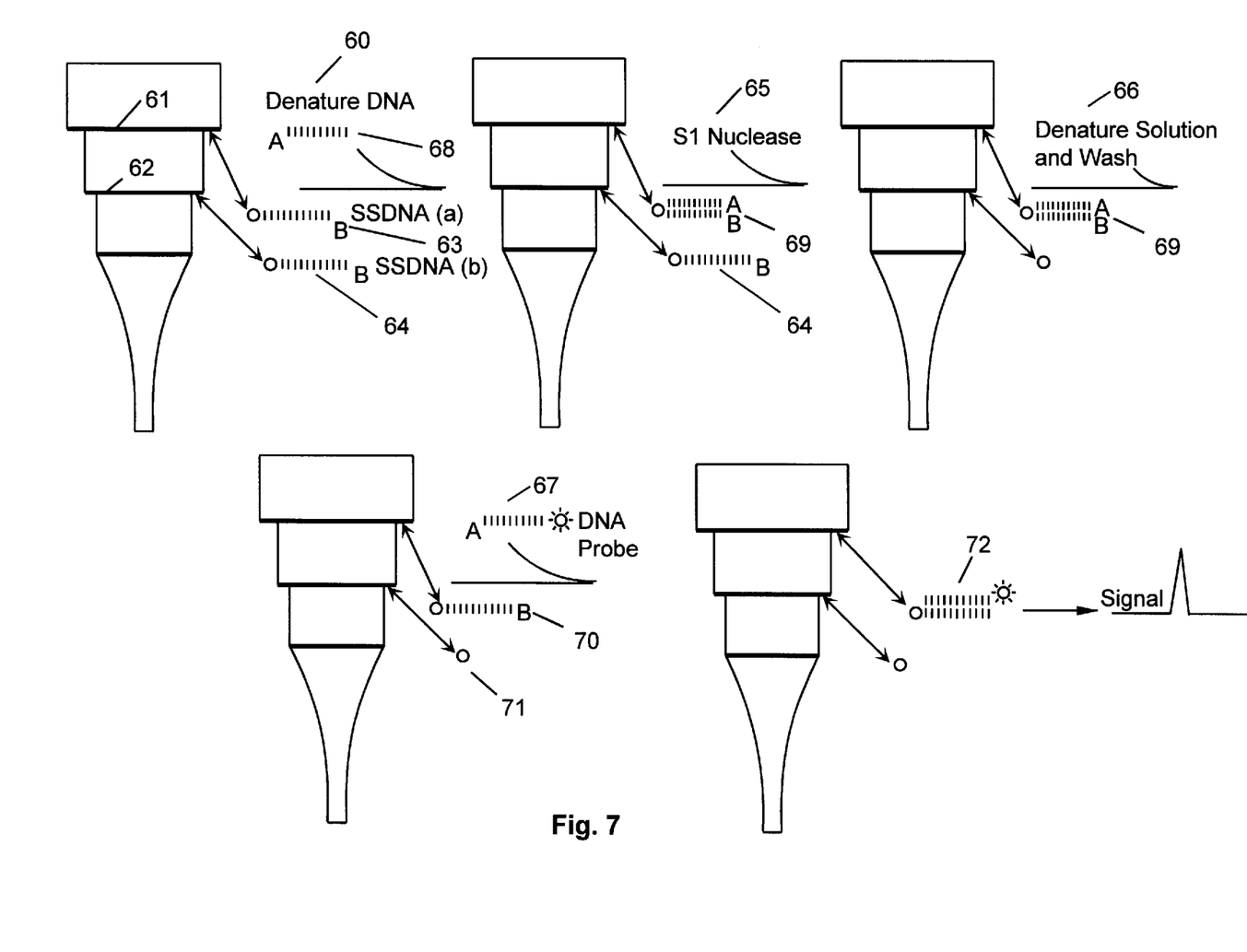
FIG. 7 illustrates a method for detecting a DNA pathogen in a sample.

Similar methods may be used for detecting DNA and RNA samples. FIG. 7 shows the use of a method with respect to DNA, which is based on a DNA probe method. In this particular embodiment it is not necessary to amplify the DNA using, for example, PCR techniques. Single strand synthetic DNA (SSDNA(a)) for the control and single strand DNA (SSDNA(b)) for the target pathogen are provided in the column on snares 61 and 62, to provide the equivalent of the capture materials (shown by 63 and 64 respectively in FIG. 7).

The patient sample is prepared so that the pathogen DNA, if present, has been isolated. The isolated pathogen DNA as well as the control DNA are denatured into single strand DNA form and then are applied to the column (shown by 60 in FIG. 7). The denatured control DNA and the pathogen DNA in the patient sample is equivalent to the control protein and the pathogen protein respectively in reference to FIGS. 5A to 5C.

The column is washed to wash away any non-binding DNA. S1 nuclease 65 is then added to the column. As is known, S1 nuclease destroys only single strand DNA. Therefore if there has been no combination of either the SSDNA(a) or SSDNA(b), the single strand DNA will be destroyed. However, if either SSDNA(a) OR SSNDA(b) has been combined to form double strand DNA, the double strand DNA will not be destroyed. Following a washing step, a further denaturing solution 66 is added to the column. This denaturing solution separates any double strand DNA into single strand DNA. The column is again washed.

Following washing, labelled DNA probes for the control and target DNA, are added to the column. Preferably, a single labelled DNA probe 67, suitable for both control and target DNA is used. Finally, the column is washed to remove any non-binding probes. The presence of any labelled DNA probes is then detected using appropriate detection means, e.g. with trigger solution and laser detectors.

In the process illustrated by FIG. 7, the denatured sample 60 only has control denatured DNA 68 therein, i.e. there is no target pathogen present. Therefore only SSDNA(a) 63 is annealed with control single strand DNA 68 to form double strand DNA 69. Because there is no denatured pathogen DNA, SSDNA(b) remains as a single strand. Therefore, after addition of S1 nuclease, SSDNA(b) is destroyed, leaving only control double strand DNA 69. Control double strand DNA 69 is denatured with wash solution 66, leaving single strand DNA 70 (which is the same as SSDNA(a)). There is no pathogen single strand DNA to denature (71). Finally a labelled DNA probe 67 is added, which forms a double strand control DNA 72, which may then be detected. In this instance, only the control DNA would be detected because there was no pathogen DNA present.

Figure 8:
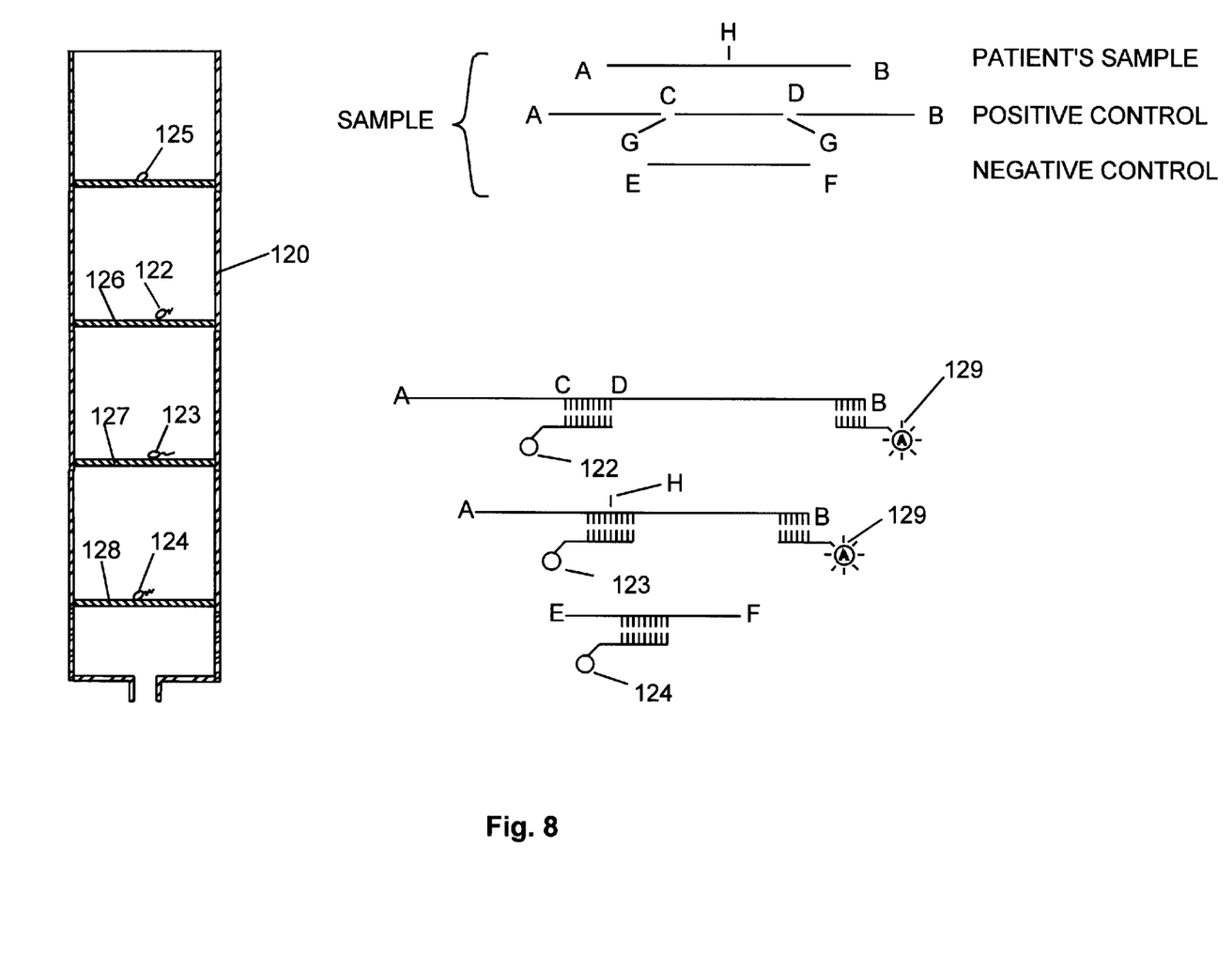
FIG. 8 illustrates another method for detecting a DNA pathogen in a sample.

Another embodiment for the DNA process is exemplified in FIG. 8. A target pathogen DNA sequence, for which detection is sought, is selected, e.g. tuberculosis DNA sequence. A mutation is formed by known techniques of insertion of a DNA sequence or deletion of a portion of the target pathogen DNA sequence. For example, in relation to FIG. 8, such a mutated target pathogen DNA is sometimes referred to as a positive control. The target pathogen has a sequence A–B. In the embodiment shown in FIG. 8, the positive control is created by inserting a synthetic DNA fragment C–D, e.g. a base of 100 nucleotides, into the target pathogen A–B, at scission point G. A negative control is also created, which is a synthetic DNA fragment E–F, of which the sequence is not present in the pathogen DNA that is sought to be detected.

For example, a fragment of pathogen DNA, of about 300 bases is selected, cloned and confirmed by DNA sequencing. Based on that cloned DNA, a small fragment of about 100 bases of non-pathogen DNA is inserted into the middle of the cloned DNA as the positive control DNA. A non-pathogen DNA of about 200 bases is also selected, cloned and confirmed by DNA sequencing and is used as a negative control DNA. When the tests are carried out, the patient sample is added to a test tube which also contains at least the positive control, and may contain the negative control.

In a variation of the above method, the positive control may have a small fragment of DNA (about 100 bases) cut away from the pathogen DNA.

For the purpose of the illustration in FIG. 8, it is assumed that the patient has the pathogen, e.g. tuberculosis, which is sought to be detected. A sample with the patient's pathogen DNA, A–B, the positive control DNA sequence A–C–D–B and the negative control DNA sequence E–F is prepared and then denatured so that the patient's sample, positive control and negative control are in single strand DNA form.

Prior to this, a test column 120 is prepared which has three single strand capture DNA materials. The positive control capture DNA 122 has a sequence which will bind specifically to the inserted DNA fragment C–D. The target pathogen capture DNA 123 has a sequence which will bind to the target DNA A–B on both sides of where the scission point is in the positive control DNA (point H in target DNA A–B). The negative control capture DNA 124 has a sequence which will bind specifically to synthetic DNA fragment E–F. AS shown in FIG. 8, positive control capture DNA 122, target capture DNA 123 and negative control capture DNA 124 are on snares 126, 127 and 128 respectively. There is a fourth snare 125 which has no DNA attached thereto. The purpose of snare 125 is for determining background "noise" in the sample. Snares 125, 126, 127 and 128 are separated longitudinally along column 120.

When performing the test for the sample, which comprises the patient's sample (target pathogen, if present) and the positive and negative controls, the sample is allowed to enter column 120. It will be understood that if there is any positive control DNA A–C–D–B in the sample, it will bind with positive control capture DNA 122 within sequence C–D, leaving a sequence adjacent B, for example, free for binding to a single strand DNA probe (129). If there is any target pathogen DNA A–B in the sample, it will bind with target capture DNA 123 about scission point H, leaving a sequence adjacent B, for example, free for binding to a single strand DNA probe (129), and if there is any negative control DNA E–F in the sample, it will bind with negative control capture DNA 124. Of course, if there is no target pathogen DNA A–B present, target capture DNA 123 will remain unbound.

After passing the sample through column 120, the snares are washed to remove excess single strand DNA which has not bound to any of the capture materials. After washing, a synthetic single strand DNA probe 129, which may bind with a sequence of the target pathogen A–B, is passed through column 120. As shown in FIG. 8, the sequence is close to position B. Probe 129 will attach itself to any positive control DNA A–C–D–B or target pathogen DNA A–B that is present, for example at the common end sequence adjacent B, as shown in FIG. 8. As the negative control DNA E–F does not share the sequence of probe 129, there is no binding of probe 129 to negative control DNA E–F. Probe 129 has a detection label thereon which is used to detect the presence thereof.

Clearly if there is no detection signal associated with snare 126, then there was no positive control DNA A–C–D–B in the sample and the results for the sample can be ignored. If there is a detection signal associated with snare 128, then the probe has bound to a material that should not have been present and the test is suspect.

As indicated hereinbefore, it is possible that the signals detected from the control DNA materials and any pathogen DNA material may be subject to some background interference caused by interaction of other materials in the sample with the snare material. The background interference can be detected from snare 125 which is independent of the control DNA materials or the pathogen DNA material. The signals obtained from detection of the control DNA materials or the pathogen DNA material can therefore be adjusted accordingly to take into account the interference.

The possible results are shown in Table I below:

TABLE 1

| Positive Control | Target | Negative Control | Result |
| --- | --- | --- | --- |
| Positive | Positive | Negative | Pathogen present |
| Positive | Negative | Negative | Pathogen not present |
| Positive | Positive | Positive | Test is false |
| Negative | Negative | Negative | Test is false |

Thus, it can be seen that the test gives a doctor a high degree of confidence of the presence or otherwise of the pathogen for which the test was made.

DNA detection may be enhanced by using the so-called PCR method, i.e. by enhancing the target sample with a PCR amplification process. With the PCR process it is possible to detect as low as one copy of a pathogen in any given sample, thus making it a very sensitive test.

In situations where re-use is permitted, when it is desired to re-use the columns in the DNA method, the columns may be cleaned merely by passing a denaturing solution through the column. This causes the capture materials to revert to the single strand capture materials. It remains then for the column to be subjected to labelled probes and trigger chemicals and any reaction detected. Normally, there would be no reactions detected and so the column may then be washed ready for re-use. If any reaction was detected, then further treatment with denaturing solution would be called for.

The present invention may also be used for RNA detection. In previously know methods, it is necessary to isolate the RNA and convert the RNA into cDNA. This leads to loss and/or degradation of the RNA. Sometimes the loss of RNA is as high as 90% or more. There is a greatly enhanced efficiency in the present test method in which very little, if any, RNA is lost. Additionally, as described in relation to the other embodiments of the invention, there is an increase in the reliability and accuracy of the test.

Figure 9:
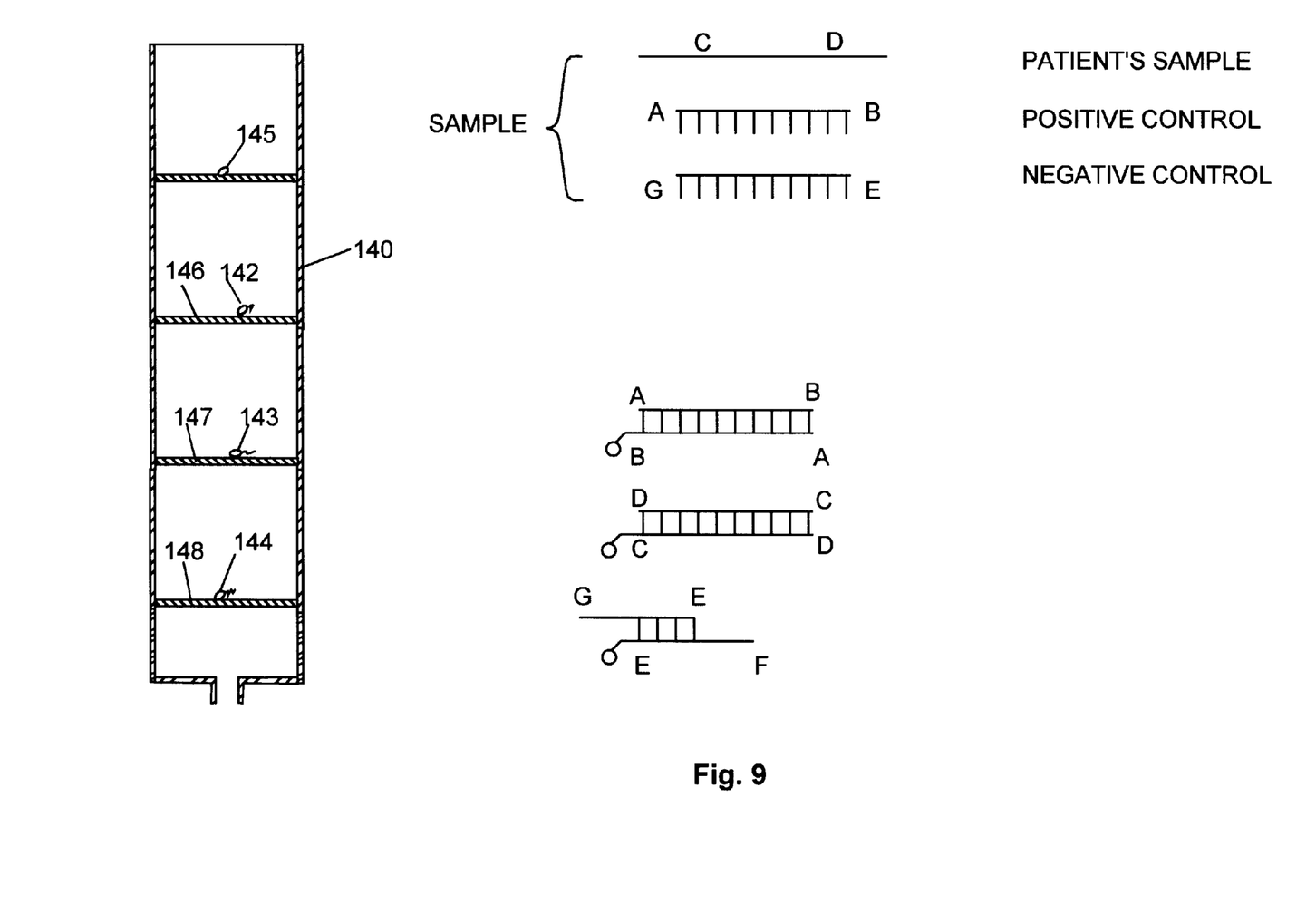
FIG. 9 illustrates a method for detecting an RNA pathogen in a sample.

An RNA pathogen detection process of the present invention is shown schematically in FIG. 9. Positive and negative controls are synthesized. For example, positive control DNA A–B and negative control DNA G–E are synthesized. The nucleotide sequences for the positive and negative controls are different to any of the sequences in the target pathogen RNA C–D.

A test column 140 is prepared which has three single strand capture DNA materials. The positive capture DNA 142 has a sequence which will bind specifically with positive control fragment A–B. The target pathogen capture DNA 143 has a sequence which will bind to the target RNA C–D if present. The negative control capture DNA 144 has a sequence E–F which will partially bind, e.g. 30–70% bind, to the negative control sequence G–E, i.e. the bound (double) strand is shorter than either of the single strand G–E sequence or the E–F sequence. As shown in FIG. 9, positive control capture DNA 142, target capture DNA 143 and negative control capture DNA 144 are on snares 146, 147 and 148 respectively. There is a fourth snare 145 which has no capture DNA attached thereto. The purpose of snare 145 is for determining background "noise" in the sample. Snares 145, 146, 147 and 148 are separated longitudinally along column 140.

When performing the test, the patient's sample (target pathogen, if present) and the positive control is allowed to enter column 140. It will be understood that if there is any positive control DNA A–B in the sample, it will bind with positive control capture DNA 142 and if there is any target pathogen RNA C–D in the sample it will bind with target capture DNA 143. Of course, if there is no target pathogen RNA C–D present, target capture DNA 143 will remain unbound.

After passing the sample through column 140, the snares are washed, to remove excess single strand material which has not bound to any of the capture materials. The negative control DNA G–E is the allowed to pass through column 140. If there is any negative control DNA G–E in the sample, it will bind with target capture DNA 144. After washing, S1 nuclease is passed through the column. As S1 nuclease destroys single strand DNA, the single strand portions of negative control DNA G–E and negative control capture E–F, which are not bound to one another, will be destroyed. This will leave a small segment of double strand DNA from the negative control capture material. Clearly, if either of the other single strand capture materials (142 or 143) have not been bound, they too will be destroyed.

The column is washed again and the now double strand materials are denatured before being washed again. Subsequently, synthetic single strand DNA probes are added to column 140 for the detection of any single strand positive control capture DNA 142 and single strand pathogen capture DNA 143 that is left in the column. The probes have detection labels thereon, which are used to detect the presence thereof.

A computer may be used to manipulate and display signals from the detectors. Additionally, a computer is preferably used to control indexing of the conveyors, activation of the introduction of reagents, control of the quantity of reagents added to the columns, and the cleaning stations if present. Use of a computer enhances the repeatability and reliability of the method. It will be understood that other control methods may be used, e.g. electromechanical methods.

Figure 10:
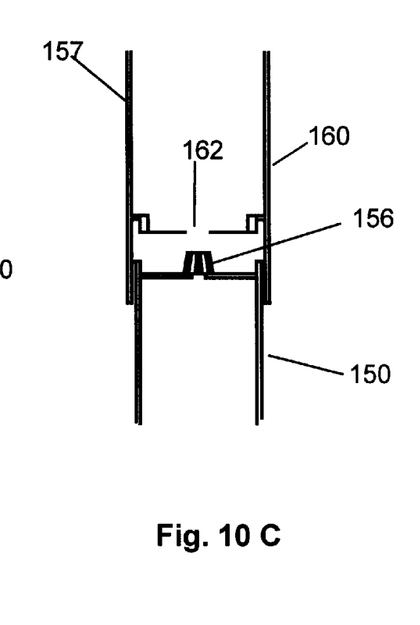
FIGS. 10A and 10B show a column and reagent dispenser prior to use, and in use, respectively.
FIG. 10C is a partial cross-sectional view of the column and reagent dispenser of FIGS. 10A and 10B just prior to connection of the two.

An apparatus for dispensing the reagents into the column is shown in FIGS. 10A to 10C. FIG. 10A shows a column 150 which comprises chambers 151, 152, 153 and 154. At the top 155 of upper chamber 151 there is a delivery spout 156 which is coaxial with the longitudinal axis of column 150. Separate from column 150 is a reagent dispenser 157 which has an open lower end 158 and an upper end 159 which may be closed or have means for the introduction of air or other gas. Inside reagent dispenser 157 is an annular disk 160 with a central bore in which there is a puncturable film 162. The reagent dispenser 157 contains reagent 161. The inner diameter of reagent dispenser 157 is marginally greater than the outer diameter of chamber 151.

In FIG. 10C, reagent dispenser 157 is situated so that annular disk 162 is just above delivery spout 156. As reagent dispenser 157 is lowered, the spout 156 is cause to puncture film 162 and allow reagent 151 to flow into column 150, as will be seen in FIG. 10B.

The Figures of the present specification show the columns in a vertical arrangement. It will be understood that the columns may be in a horizontal alignment. For example, with the chambers of a column may be placed side-by-side.

Figure 11:
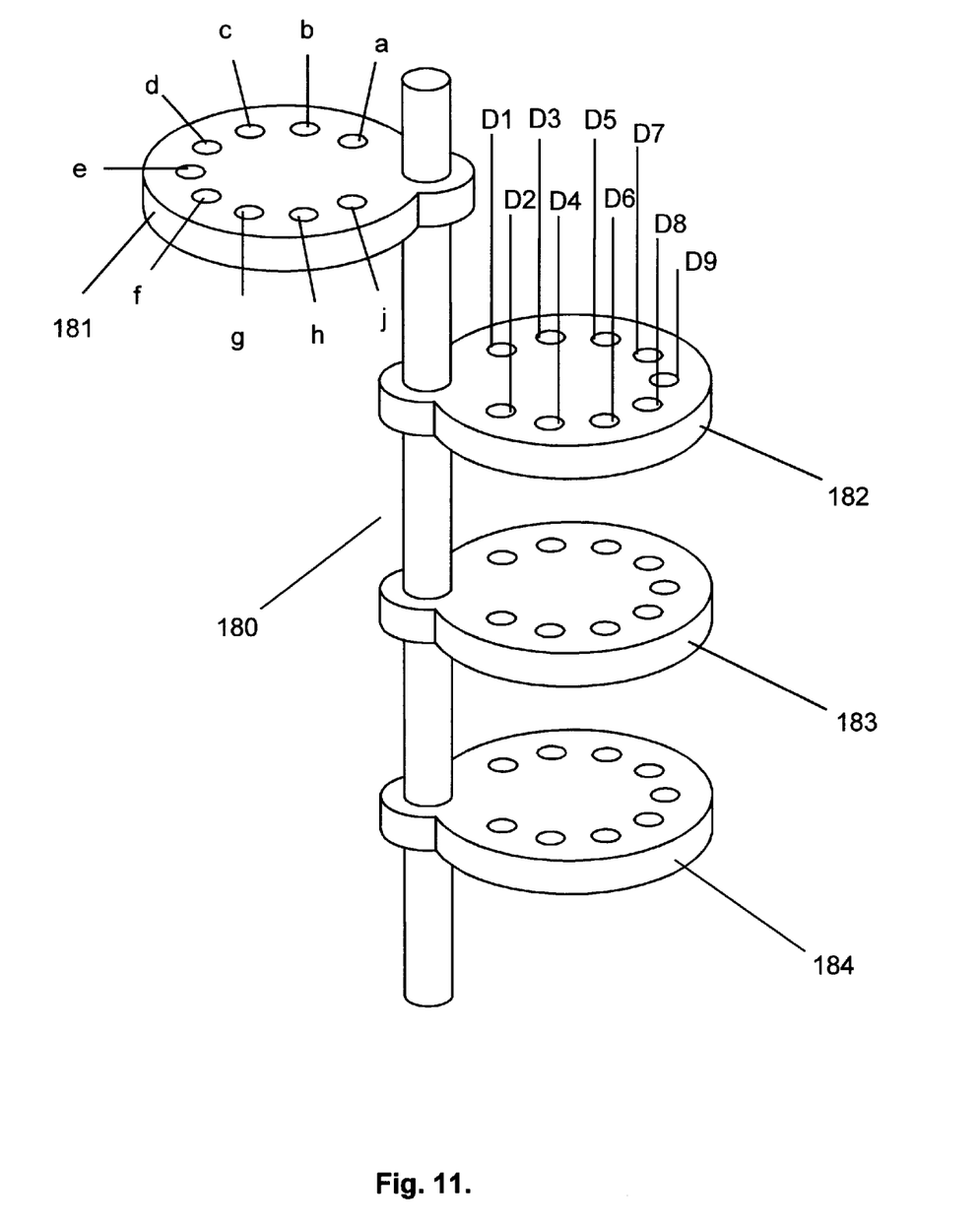
FIG. 11 shows a column with a plurality of snares in the same plane, transverse to the longitudinal axis of the column.

In FIG. 11, there is a stem 180 with a plurality of snare trays 181, 182, 183 and 184. Each snare tray has a plurality of snares thereon, e.g. a, b, c, d, e, f, g, h and j on tray 181, which may be viewed as equivalent to a column. Snares a and b for example may be for detection of positive and negative control materials, leaving snares c to j for detection of seven different pathogen materials. The snares may be subjected to methods of binding, labelling and detection substantially as described hereinbefore. Because the snares on any one tray are in a plane transverse to the longitudinal direction of the stem 180, detection is best performed by placing the detectors above the trays. For example, detection may be made with detectors D1 to D9. In the embodiment shown in FIG. 11, it will be understood that detection of the materials on snare 181 has been completed and tray 181 has been swung out of the way of detectors D1 to D9. Detectors D1 to D9 are in position for detecting capture and labelled materials on the snares of tray 182. Thus each tray is adaptable to detection of a large number of materials, e.g. pathogens, with a single tray. It will be appreciated that the chambers in the columns shown in FIGS. 4 and 5A may have multiple snares at one or more levels, i.e. be in a plane which is transverse to the longitudinal axis, much as shown in tray 181.

As indicated herein, the method of the present invention has wide applicability. Areas of applicability include research and diagnosis relating to cancer, auto-immune diseases, infectious diseases, haemostasis and vetinary medicine. For example, the DNA method of the present invention may be used for diagnosis of N. gonorrhoea, H. ducreyi, trepona pallidum, human papillomavirus (HPV), herpes simplex virus (HSV), molluscum contagiosum (MC), trichomonas vaginalis and the RNA method may be used for diagnosis of human immunodeficiency virus (HIV).

It will be understood that multiple tests can be carried out in a single column merely by the addition of additional snares, capture materials and detection materials. For example, the test may be used simultaneously for certain proteins, DNA fragments and RNA fragments.

To demonstrate the improved sensitivity of the present method, a comparison was made between it and a known UV detection method.

EXAMPLE

A positive PCR DNA sample was dye labelled and prepared for detection of the DNA. Part of the sample (aliquots 1A and 1B) was retained for direct analysis. The remainder of the sample was diluted ten times, and part of this first-diluted sample (aliquots 2A and 2B) was retained for analysis. The remainder of the first-diluted sample was diluted ten times to form a second-diluted sample. A part of this second-diluted sample (aliquots 3A and 3B) was retained for analysis. The remainder of the second-diluted sample was diluted ten times to form a third-diluted sample. A part of this third-diluted sample (aliquots 4A and 4B) was retained for analysis. The remainder of the third-diluted sample was diluted ten times to form a fourth-diluted sample. A part of this fourth-diluted sample (aliquots 5A and 5B) was retained for analysis. The remainder of the fourth-diluted sample was diluted ten times to form a fifth-diluted sample. A part of this fifth-diluted sample (aliquots 6A and 6B) was retained for analysis. Aliquots 1A, 2A, 3A, 4A, 5A and 6A were analyzed using standard UV detection with visual interpretation of the results. Aliquots 1A, 2A and 3A gave positive identifications, whereas aliquots 4A, 5A and 6A gave negative indications, even though the DNA was present. Aliquots 1B, 2B, 3B, 4B, 5B and 6B were analyzed by the present invention, substantially according to the method of FIG. 7, with a laser detector and computerized display of the signals. Each of aliquots 1B to 6B gave positive identifications.

What is claimed is:

1. A method for detecting the presence of at least two predetermined known materials in a test sample, wherein at least one of the predetermined known materials is a control material, wherein the method comprises:
   a) introducing the test sample, which contains at least one control material, into a test column which has a snare for each predetermined known material, each snare having a capture material specific to the associated predetermined known material, which will bind with the associated predetermined known material to form a bound material;
   b) washing the test column to remove any materials which have not been bound to the capture materials; and
   c) detecting the presence of bound materials on each of the snares.

2. A method according to claim 1 wherein step c) comprises adding a label material for each of the bound materials to form labelled bound materials and then detecting the presence of the labelled bound materials.

3. A method according to claim 2 for detecting the presence of at least two predetermined known DNA materials, wherein the capture materials are single strand capture DNA materials and the test sample has been denatured so that any predetermined known DNA materials are in single strand form prior to addition to the test column, and detection of the bound materials is accomplished by adding a label material for each of the bound materials to form labelled bound materials and then detecting the labelled bound materials.

4. A method for detecting the presence of at least two predetermined DNA materials, wherein at least one of the predetermined known DNA materials is a control material which has a control DNA segment and one of the predetermined known DNA materials has a DNA segment for which detection is being sought, said method comprising the steps of:
   i) denaturing the predetermined known DNA materials;
   ii) adding a sample, which contains at least one denatured control DNA segment, to a column which has at least one control snare and at least one test snare, one of the control snares having thereon a first control single strand capture DNA segment for binding to the denatured control DNA segment, and one of the test snares having thereon a test single strand capture DNA segment for detecting the denatured test DNA segment for which detection is being sought, so that the denatured control DNA segment binds with the first control single strand capture DNA segment to form a double strand control DNA segment, and any denatured test DNA present binds with the test single strand capture DNA segment to form a double strand test DNA segment;
   iii) adding a wash solution to the column to remove any unbound DNA;
   iv) adding S1 nuclease to the column to destroy any single strand DNA;
   v) adding a wash solution and a denaturing solution to the column to re-form the first control single strand capture DNA segment and the test single strand capture DNA segment;
   vi) adding DNA probes to provide detectable labels for the first control single strand capture DNA segment and the test single strand capture DNA segment formed in step v);
   vii) adding a wash solution to the column to remove any unbound DNA probe;
   viii) adding a substrate which reacts with the labels to give off detectable signals; and
   ix) detecting any signals from the control and test snares.

5. A method for detecting the presence of at least two predetermined DNA materials, wherein at least one of the predetermined known DNA materials is a control material, and one of the predetermined known DNA materials has a DNA segment for which detection is being sought, said method comprising the steps of:
   i) preparing a positive control DNA material from a DNA material for which detection is sought, by a process selected from the group consisting of a) inserting a control DNA sequence into the DNA material at a predetermined scission point in the first DNA material and b) removing a small fragment of DNA from the first DNA material at a predetermined scission point;
   ii) denaturing a test sample which contains at least the positive control DNA material;
   iii) adding the sample, which contains denatured positive control DNA material, to a test column which has at least one control snare and at least one test snare, one of the control snares having thereon a first control single strand capture DNA segment for binding to a portion of the positive control DNA material, and one of the test snares having thereon a test single strand capture DNA segment for detecting denatured test DNA segment for which detection is being sought, so that the positive control DNA material binds with the first control single strand capture DNA segment to form a bound positive control DNA material which also has an unbound single strand segment, and any denatured test DNA present binds with the test single strand capture DNA segment to form a bound test DNA material which also has an unbound single strand segment;
   iv) adding a wash solution to the column to remove any unbound DNA;
   v) adding DNA probes to provide detectable labels for attachment to the unbound segment of the bound positive control DNA material and the unbound segment of the bound test DNA material formed in step iii);
   vi) adding a wash solution to the column to remove any unbound DNA probe;
   vii) adding a substrate which reacts with the labels to give off detectable signals; and
   viii) detecting any signals from the control and test snares.

6. A method according to claim 5 wherein the unbound segment of the bound positive control DNA material and the unbound segments of the bound test DNA material have the same sequence, and wherein the DNA probe is a single common DNA probe used for attachment to both the unbound segment of the bound positive control DNA material and the unbound segment of the bound test DNA material.

7. A method according to claim 5 wherein steps i) and ii) include preparation of a denatured negative control DNA material, wherein the negative control DNA material has a DNA segment which is different from the test DNA segment and different from the positive DNA segment; and wherein in step iii) the sample also contains the denatured negative control DNA material, said test column also having a control snare having thereon a second control single strand capture DNA segment for binding to the negative control DNA material, so that the negative control DNA material binds with the second control single strand capture segment to form a bound negative control DNA material.

8. A method according to claim 1 wherein one of the predetermined known materials is a pathogen for which detection is being sought, comprising the steps of:
   i) adding a sample, which contains at least one control material, to a column which has at least one control snare and at least one test snare, each of the control snares having thereon a first capture antibody for binding to the control material, and each of the test snares having thereon a pathogen capture antibody for binding to the pathogen for which detection is being sought, so that the control material binds with the first capture antibody to form a bound control material, and any pathogen present binds with the pathogen capture antibody to form a bound pathogen;
   ii) adding a wash solution to the column to remove any unbound control material and any unbound pathogens;
   iii) adding a sufficient amount of primary antibodies to the column, to bind with the control material and any bound pathogens, said primary antibodies having labels thereon;
   iv) adding a wash solution to the column to remove any unbound primary antibodies;
   v) adding a substrate which reacts with the labels to give off a detectable signal; and
   vi) detecting any detectable signals from the labelled and bound control material and from any labelled and bound pathogen.

9. A column for analysis of at least one pathogen in which the column has at least two snares, one of said snares having thereon a first control capture material for detecting the presence of a first control material, and the other of said snares having thereon a pathogen capture material for detecting a pathogen for which detection is being sought, and wherein said snares are separate spatially one from another so that said snares are not in contact with one another.

10. A column according to claim 9 wherein the snares are separated longitudinally along the column.

11. A column according to claim 9 wherein the snares are separated radially about a longitudinal axis of the column.

12. A column according to claim 9 wherein the column has a snare having thereon a first control material, and a plurality of snares each having thereon a pathogen capture material wherein the pathogen capture materials are different from one another, and wherein the snares are separate spatially one from another so that said snares are not in contact with one another.

13. A column according to claim 9 wherein the column has a snare, having thereon a first control capture material, at least one snare having thereon a pathogen capture material and a snare having thereon a second control capture material for detecting the presence of a second control material.

14. A column according to claim 9 wherein the column comprises at least two chambers, at least one of the chambers containing a snare with a first control capture material for detecting the presence of a first control material, and at least one of the chambers containing a pathogen capture material for detecting a pathogen for which detection is being sought, each of said chambers having connecting means to connect the chambers in a predetermined sequence along the column.

15. A kit which comprises i) a column for analysis of at least one pathogen in which the column has at least two snares, and said snares are separate spatially one from another so that said snares are not in contact with one another, one of said snares having thereon a first control capture material for detecting the presence of a first control material, and the other of said snares having thereon a pathogen capture material for detecting a pathogen for which detection is being sought, ii) reagents for detecting the presence of materials selected from the group consisting of a) reagents for detecting the presence of the control pathogen and the test pathogen, and b) reagents for detecting the presence of the first control capture material and the pathogen capture material after the first control capture material and the pathogen capture material have been bound and then unbound from the first control material and the pathogen material.

* * * * *